(12) United States Patent
Ben Oren et al.

(10) Patent No.: US 12,193,736 B2
(45) Date of Patent: *Jan. 14, 2025

(54) APPARATUS AND METHODS FOR RESECTING AND/OR ABLATING AN UNDESIRED TISSUE

(71) Applicant: Eximo Medical Ltd., Rehovot (IL)

(72) Inventors: Ilan Ben Oren, Modi'in (IL); Yoel Zabar, Nes Ziona (IL); Oren Meshulam Stern, Shilo (IL)

(73) Assignee: EXIMO MEDICAL LTD., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/318,313

(22) Filed: May 16, 2023

(65) Prior Publication Data

US 2023/0363819 A1 Nov. 16, 2023

Related U.S. Application Data

(63) Continuation of application No. 16/094,137, filed as application No. PCT/IL2017/050498 on May 5, 2017, now Pat. No. 11,684,420.

(Continued)

(51) Int. Cl.
*A61B 18/24* (2006.01)
*A61B 18/14* (2006.01)
(Continued)

(52) U.S. Cl.
CPC .......... *A61B 18/24* (2013.01); *A61B 18/1492* (2013.01); *A61B 2018/0016* (2013.01);
(Continued)

(58) Field of Classification Search
CPC ..... A61B 18/24; A61B 18/1492; A61B 34/30; A61B 2018/0066; A61B 2018/2272;
(Continued)

(56) References Cited

U.S. PATENT DOCUMENTS

| 4,641,912 A | 2/1987 | Goldenberg |
| 4,732,448 A | 3/1988 | Goldenberg |

(Continued)

FOREIGN PATENT DOCUMENTS

| CA | 3017252 C | 12/2019 |
| CA | 3105728 A1 | 1/2020 |

(Continued)

OTHER PUBLICATIONS

International Preliminary Report on Patentability issued in App. No. PCT/IB2022/061041, dated May 30, 2024, 17 pages.

*Primary Examiner* — Rex R Holmes
(74) *Attorney, Agent, or Firm* — Kevin P. Radigan, Esq.; Heslin Rothenberg Farley & Mesiti P.C.

(57) ABSTRACT

There is provided herein a catheter for resecting an undesired tissue from a body of a subject, the catheter comprising a tip section in a shape of a cylinder or a cylinder's sector having a central longitudinal axis, the tip section comprising: a central longitudinal lumen; a first set of optical fibers configured to transmit laser radiation outside a distal extremity of the tip section, in a direction parallel to the central longitudinal axis; a second set of optical fibers configured to transmit laser radiation, transversely to the central longitudinal axis; wherein the first set of optical fibers and the second set of optical fibers are selectively operable to resect and/or ablate the undesired tissue.

19 Claims, 11 Drawing Sheets

Related U.S. Application Data

(60) Provisional application No. 62/332,106, filed on May 5, 2016.

(51) Int. Cl.
    A61B 18/00        (2006.01)
    A61B 18/22        (2006.01)
    A61B 34/30        (2016.01)

(52) U.S. Cl.
    CPC .............. *A61B 2018/0019* (2013.01); *A61B 2018/00208* (2013.01); *A61B 2018/00577* (2013.01); *A61B 2018/00589* (2013.01); *A61B 2018/00601* (2013.01); *A61B 2018/00607* (2013.01); *A61B 2018/00642* (2013.01); *A61B 2018/0066* (2013.01); *A61B 2018/00904* (2013.01); *A61B 2018/00982* (2013.01); *A61B 2018/2211* (2013.01); *A61B 2018/2261* (2013.01); *A61B 2018/2272* (2013.01); *A61B 34/30* (2016.02); *A61B 2034/301* (2016.02)

(58) Field of Classification Search
    CPC .... A61B 2018/00642; A61B 2034/301; A61B 2018/00208; A61B 2018/00904; A61B 2018/2261; A61B 2018/00601; A61B 2018/00607; A61B 2018/00982; A61B 2018/2211; A61B 2018/0016; A61B 2018/0019; A61B 2018/00577; A61B 2018/00589
    See application file for complete search history.

(56) References Cited

U.S. PATENT DOCUMENTS

| | | |
|---|---|---|
| 6,547,757 B1 | 4/2003 | Kranz |
| 7,931,659 B2 | 4/2011 | Bose |
| 7,976,533 B2 | 7/2011 | Larsson |
| 8,246,580 B2 | 8/2012 | Hopkins |
| 8,366,735 B2 | 2/2013 | Bose |
| 8,460,312 B2 | 6/2013 | Bose |
| 8,486,051 B2 | 7/2013 | Larsson |
| 8,915,896 B2 | 12/2014 | Sanders |
| 9,119,656 B2 | 9/2015 | Bose |
| 9,119,907 B2 | 9/2015 | Sherman |
| 9,199,011 B2 | 12/2015 | Locke |
| 9,655,633 B2 | 5/2017 | Leynov |
| 9,662,478 B2 | 5/2017 | Browd |
| 9,681,882 B2 | 6/2017 | Garrison |
| 9,820,761 B2 | 11/2017 | Garrison |
| 9,844,485 B2 | 12/2017 | Locke |
| 9,855,374 B2 | 1/2018 | Sherman |
| 9,864,140 B2 | 1/2018 | Adler |
| 9,883,877 B2 | 2/2018 | Look |
| 9,925,316 B2 | 3/2018 | Sanders |
| 10,166,375 B2 | 1/2019 | Browd |
| 10,201,315 B2 | 2/2019 | Peatfield |
| 10,226,263 B2 | 3/2019 | Look |
| 10,391,275 B2 | 8/2019 | Burnett |
| 10,702,292 B2 | 7/2020 | Look |
| 10,716,583 B2 | 7/2020 | Look |
| 10,722,253 B2 | 7/2020 | Deville |
| 10,765,592 B2 | 9/2020 | Locke |
| 10,835,647 B2 | 11/2020 | Sherman |
| 10,835,711 B2 | 11/2020 | Yang |
| 10,993,731 B2 | 5/2021 | Leynov |
| 11,051,832 B2 | 7/2021 | Look |
| 11,197,683 B1 | 12/2021 | Teigen |
| 11,247,030 B2 | 2/2022 | Browd |
| 11,259,821 B2 | 3/2022 | Buck |
| 11,317,787 B2 | 5/2022 | Hillman |
| 11,337,712 B2 | 5/2022 | Teigen |
| 11,357,951 B2 | 6/2022 | Burnett |
| 11,369,435 B2 | 6/2022 | Khan |
| 11,400,255 B1 | 8/2022 | Chou |
| 11,406,402 B2 | 8/2022 | Deville |
| 11,432,835 B2 | 9/2022 | Shaffer |
| 11,464,528 B2 | 10/2022 | Brady |
| 11,471,582 B2 | 10/2022 | Yee |
| 11,490,909 B2 | 11/2022 | Look |
| 11,497,521 B2 | 11/2022 | Mallaby |
| 11,547,426 B2 | 1/2023 | Deville |
| 11,835,707 B2 | 12/2023 | Liang |
| 2002/0095087 A1 | 7/2002 | Mourad |
| 2003/0171691 A1 | 9/2003 | Casscells |
| 2004/0236228 A1 | 11/2004 | Stoltz |
| 2006/0229515 A1 | 10/2006 | Sharareh |
| 2007/0016068 A1 | 1/2007 | Grunwald |
| 2007/0073268 A1 | 3/2007 | Goble |
| 2007/0149985 A1 | 6/2007 | Cole |
| 2008/0082091 A1 | 4/2008 | Rubtsov |
| 2008/0177183 A1 | 7/2008 | Courtney |
| 2009/0048607 A1 | 2/2009 | Rockley |
| 2011/0060300 A1 | 3/2011 | Weig |
| 2013/0310680 A1 | 11/2013 | Werahera |
| 2014/0188062 A1 | 7/2014 | James |
| 2015/0238091 A1 | 8/2015 | Iyer |
| 2015/0320480 A1 | 11/2015 | Cosman, Jr. |
| 2016/0029902 A1* | 2/2016 | Smith ................ A61B 1/3137 600/478 |
| 2016/0135883 A1 | 5/2016 | Herscher |
| 2017/0100142 A1 | 4/2017 | Look |
| 2018/0028794 A1 | 2/2018 | Browd |
| 2018/0104390 A1 | 4/2018 | Kilcran |
| 2018/0207397 A1 | 7/2018 | Look |
| 2019/0216476 A1 | 7/2019 | Barry |
| 2019/0290815 A1 | 9/2019 | Antonicelli |
| 2019/0343445 A1 | 11/2019 | Burnett |
| 2020/0022711 A1 | 1/2020 | Look |
| 2020/0179576 A1 | 6/2020 | Wood |
| 2020/0179578 A1 | 6/2020 | Look |
| 2020/0206457 A1 | 7/2020 | Boling |
| 2020/0281610 A1 | 9/2020 | Look |
| 2020/0289722 A1 | 9/2020 | Culbert |
| 2020/0337772 A1 | 10/2020 | Ben-Oren |
| 2021/0038306 A1 | 2/2021 | McLoughlin |
| 2021/0069467 A1 | 3/2021 | Garrison |
| 2021/0093756 A1 | 4/2021 | Sherman |
| 2021/0109340 A1 | 4/2021 | Kaicheng |
| 2021/0315598 A1 | 10/2021 | Buck |
| 2022/0008090 A1 | 1/2022 | Look |
| 2022/0031930 A1 | 2/2022 | Downey |
| 2022/0096104 A1 | 3/2022 | Ogle |
| 2022/0152345 A1 | 5/2022 | Simiele |
| 2022/0152346 A1 | 5/2022 | Burnett |
| 2022/0176031 A1 | 6/2022 | Cheng |
| 2022/0193366 A1 | 6/2022 | Cheng |
| 2022/0211437 A1 | 7/2022 | Ben-Oren |
| 2022/0218365 A1 | 7/2022 | Deville |
| 2022/0257268 A1 | 8/2022 | Culbert |
| 2022/0280171 A1 | 9/2022 | Teigen |
| 2022/0338887 A1 | 10/2022 | Nair |
| 2022/0339338 A1 | 10/2022 | Nair |
| 2022/0339339 A1 | 10/2022 | Nair |
| 2022/0378443 A1 | 12/2022 | Look |
| 2022/0378450 A1 | 12/2022 | Culbert |
| 2022/0379081 A1 | 12/2022 | Look |
| 2022/0379082 A1 | 12/2022 | Look |
| 2022/0379083 A1 | 12/2022 | Look |
| 2022/0379084 A1 | 12/2022 | Look |
| 2022/0379085 A1 | 12/2022 | Look |
| 2022/0379086 A1 | 12/2022 | Look |
| 2022/0387052 A1 | 12/2022 | Look |
| 2022/0387752 A1 | 12/2022 | Look |
| 2022/0387753 A1 | 12/2022 | Look |
| 2023/0026412 A1 | 1/2023 | Teigen |
| 2023/0099283 A1 | 3/2023 | Deville |
| 2023/0100426 A1 | 3/2023 | Deville |
| 2023/0301708 A1 | 9/2023 | Mickelsen |

(56) References Cited

U.S. PATENT DOCUMENTS

2023/0329780 A1  10/2023  Liu
2023/0408329 A1  12/2023  Zabar

FOREIGN PATENT DOCUMENTS

| CN | 112533550 | A  | 3/2021  |
|----|-----------|----|---------|
| EP | 3423124   | A4 | 10/2019 |
| EP | 3806757   | A4 | 5/2022  |
| JP | 2021532850| A  | 12/2021 |
| KR | 20210035811| A | 4/2021  |
| WO | 03057060  | A1 | 7/2003  |
| WO | 2017155994| A1 | 9/2017  |
| WO | 2018019829| A1 | 2/2018  |

\* cited by examiner

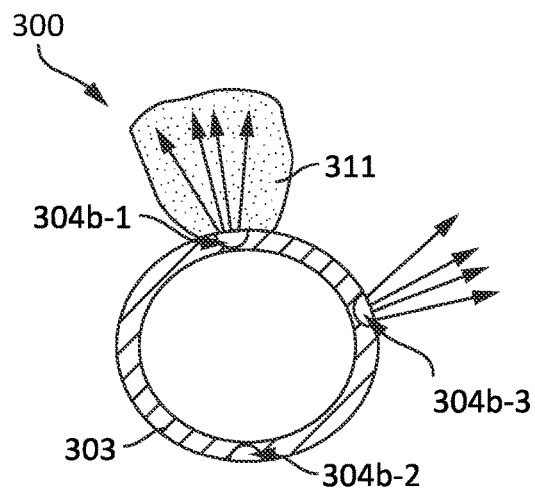
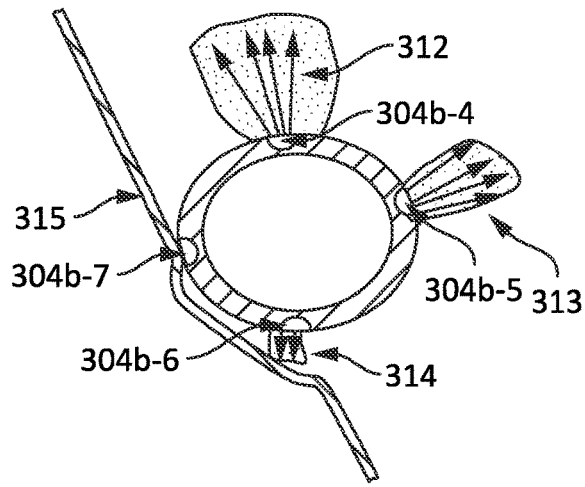
FIG. 3B
FIG. 3C

600

600

600

APPARATUS AND METHODS FOR RESECTING AND/OR ABLATING AN UNDESIRED TISSUE

CROSS-REFERENCE TO RELATED APPLICATIONS

This application is a continuation of U.S. patent application Ser. No. 16/094,137 filed Oct. 16, 2018, and issued Jun. 27, 2023, as U.S. Pat. No. 11,684,420 B2, which is a United States national stage entry under 35 U.S.C. 371 of International Application No. PCT/IL2017/050498 filed May 5, 2017, which claims the benefit of U.S. Provisional Application No. 62/332,106, filed May 5, 2016, the disclosures of which are hereby incorporated by reference in their entireties.

FIELD OF THE INVENTION

Embodiments of the disclosure relate to device, system, and method for tissue resection.

BACKGROUND

Radio-Frequency Ablation (RFA) is a minimally invasive medical procedure that utilizes electrical energy to thermally ablate tumor cells. Similarly, microwave energy laser is used and laser ablation.

Management of tumor and other suspected lesions in the pancreas by thermal ablation that triggers tissue necrosis is known to be problematic as collateral damage of healthy surrounding tissue can be very risky due to the friable pancreatic parenchyma, the fear of pancreatitis and extravasation of pancreatic enzymes. This together with the challenge to control impact in different anatomies and the heterogeneity of the tissue that makes thermal impact difficult to predict and need to avoid damage to vessel, duodenum, etc. limits utility of tools such as Radio-Frequency (RF) and microwave ablation. Reported complications of RFA in pancreas include gastro-intestinal haemorrhage, pancreatic fistula, biliary leak, portal vein thrombosis, pancreatic pseudocyst and sepsis. Similarly, many complications such as hemorrhage, injuries to bowel and biliary tree, vascular thrombosis and hepatic infarction, biliary strictures and more have been reported for image guided thermal ablation in the liver.

There are attempts to find new solutions for endoscopic ultrasound EUS guided ablation. Attempts to use Nd:YAG ablation of pancreatic tissue using optical fibers show some promise but impact was limited.

Another limitation of common techniques is to obtain biopsies to analyze lesions in pancreas, liver etc. Adequate sample can enable reliable histology analysis of lesions/surrounding tissue, genetic analysis, etc. One of the limitation of prior art tools is to collect large enough samples without risk of bleeding and/or spread tumor cells. Similar risks and limitations of technologies for ablation of tumors and/or collection of reliable biopsy samples are known in the area of liver tumors management.

There is an attempt to detect tumors when are small. Tumors in sizes in the range of a few centimeters, in the liver and pancreas, may be managed and enable to improve patient prognosis if resected and ablated effectively while minimizing collateral damage. There is thus a need in the art for safe and effective ablation techniques, using catheters with diameters of a few millimeters in diameter.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

According to some embodiments, there is provided a catheter for resecting an undesired tissue from a body of a subject, the catheter comprising a tip section in a shape of a cylinder or a cylinder's sector having a central longitudinal axis, the tip section comprising: a central longitudinal lumen; a first set of optical fibers configured to transmit laser radiation outside a distal extremity of the tip section, in a direction parallel to the central longitudinal axis; a second set of optical fibers configured to transmit laser radiation, transversely to the central longitudinal axis; wherein the first set of optical fibers and the second set of optical fibers are selectively operable to resect and/or ablate the undesired tissue.

According to some embodiments, the first set of optical fibers and the second set of optical fibers may be independently and/or selectively operable according to an image of the undesired tissue.

According to some embodiments, the first set of optical fibers may be configured to resect tissue in front of the first set of optical fibers to reach tissue that needs to be removed.

According to some embodiments, each one or each subset of optical fibers of the second set of optical fibers may be independently and/or separately controllable according to an image of the undesired tissue so as to selectively ablate the undesired tissue or parts thereof.

According to some embodiments, the catheter may further be configured to facilitate extraction of the resected undesired tissue or parts thereof in a form that allows laboratory testing thereof.

According to some embodiments, the first set of optical fibers may be positioned along and parallel to the central longitudinal axis and extends to the distal extremity of the tip section.

According to some embodiments, the second set of optical fibers may be positioned along and parallel to the central longitudinal axis and extends proximally to the distal extremity of the tip section.

According to some embodiments, the catheter may further include a cutter comprising one or more blades configured to cut the undesired tissue, wherein the cutter is positioned outside optical paths of the laser radiation transmitted from the first set and the second set of optical fibers. The cutter may be formed from a distal edge of a wall of the tip section or affixed to the distal edge of the wall of the tip section. The cutter' wall may have sharp distal edges.

According to some embodiments, the laser radiation may be pulsed radiation.

According to some embodiments, the first set of optical fibers is operatively coupled to a first laser and the second set of optical fibers may operatively be coupled to a second laser and/or laser diodes.

According to some embodiments, the second set of optical fibers may operatively be coupled to a Multiplex laser configured to transmit laser radiation at different wavelengths, intensities and/or pulses frequencies.

According to some embodiments, there is provided a system for resecting an undesired tissue from a body of a subject, the system comprising: a catheter comprising a tip section in a shape of a cylinder's sector having a central longitudinal axis, the tip section comprising: a central longitudinal lumen; a first set of optical fibers configured to transmit laser radiation outside a distal extremity of the tip section, in a direction parallel to the central longitudinal axis; and a second set of optical fibers configured to transmit laser radiation, transversely to the central longitudinal axis; and a processor configured to selectively control at least one parameter of laser radiation transmitted at least by the second set of optical fibers based on a location and/or a 3D image of the undesired tissue, obtained prior to and/or during the resection of the undesired tissue. According to some embodiments, the at least one parameter may include wavelength, power, intensity, pulse frequency or any combination thereof.

According to some embodiments, the processor may further be configured to selectively activate each one or each subset of optical fibers of the second set of optical fibers. The processor may further be configured to determine advancement speed/rate of the catheter.

According to some embodiments, the system may further include an extraction mechanism configured to facilitate extraction of the resected undesired tissue or part thereof in a form that allows laboratory testing of the undesired tissue.

According to some embodiments, the system may further include a MultiPlex laser operably coupled at least to the second set of optical fibers.

According to some embodiments, the system may further include a first laser operably coupled to the first set of optical fibers and a second laser operatively coupled to the second set of optical fibers.

According to some embodiments, the system may further include a first laser operably coupled to the first set of optical fibers and at least two laser diodes operatively coupled to the optical fibers of the second set of optical fibers.

According to some embodiments, the system may further include a cutter comprising one or more blades configured to cut a tissue, wherein the cutter is positioned outside optical paths of the laser radiation transmitted by the first set and the second set of optical fibers.

According to some embodiments, the system may further include a cutter comprising one or more blades configured to cut a tissue, wherein the cutter made of material that is transparent to the radiation emitted from the second set of fibers.

According to some embodiments, there is provided a method for resecting an undesired tissue from a body of a subject, the method comprising: utilizing a catheter having a longitudinal axis and a first and a second set of optical fibers, transmitting laser radiation through the first set of optical fibers to a first area of the undesired tissue, thereby causing non-thermal ablation and/or resection thereof, wherein the radiation is transmitted at a first direction essentially parallel to the longitudinal axis; and transmitting laser radiation through the second set of optical fibers to a second area of the undesired tissue thereby causing thermal or non-thermal ablation thereof, wherein the radiation from the second set of optical fibers is transmitted at a second direction, non-parallel to the first direction; and wherein at least one parameter of the laser radiation transmitted by the second optical fiber is controllable. The method may further include utilizing a cutter positioned on the catheter to cut through the undesired tissue, thereby resecting at least a part of the undesired tissue. According to some embodiments, transmitting the first laser radiation and the cutting may be conducted simultaneously. According to some embodiments, according to some embodiments, transmitting the first laser radiation and the cutting may be conducted intermittently.

According to some embodiments, the method may further include obtaining an image (for example, a 3D image) of the undesired tissue.

According to some embodiments, the method may further include selectively activating each one or each subset of optical fibers of the second set of optical fibers based on an interpretation of the image of the undesired tissue.

According to some embodiments, the at least one parameter may include wavelength, power, intensity, pulse frequency or any combination thereof or any other parameter.

According to some embodiments, the method may further include extracting the resected undesired tissue in a form that allows laboratory testing of the undesired tissue or parts thereof.

According to some embodiments, the method may further include advancing the catheter trough a path within, in proximity to the undesired tissue or in a tissue in order to reach the undesired tissue.

More details and features of the current invention and its embodiments may be found in the description and the attached drawings.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. The figures are listed below:

FIGS. 3B and 3C are distal end views of the cylindrical tip section of FIG. 3A, according to an exemplary embodiment of the current invention;

DETAILED DESCRIPTION

Figure 1:
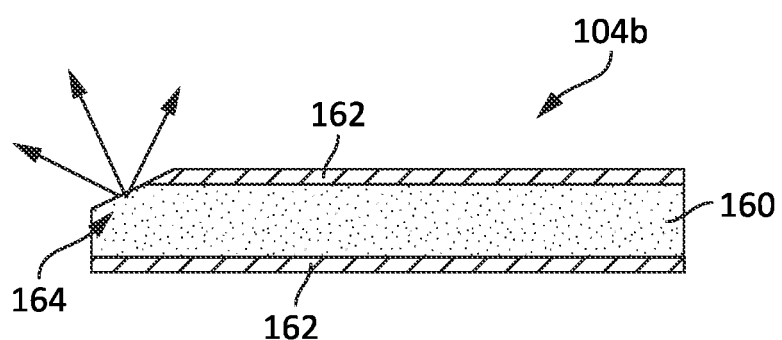
FIG. 1 schematically depicts a modified optical fiber, according to an exemplary embodiment of the current invention.

Disclosed herein are device, system, and a method for resection of undesired tissue such as lesions or tumors from the body of a subject. Advantageously, the device, system and method disclosed herein, according to some embodiments, may be used for resection of undesired tissue such as lesions or tumors from body organs such as pancreas and liver.

An aspect of some embodiments relates to a catheter and methods for using the same in resection of lesions or tumors in a body organ. The catheter may be introduced to a target site within a body organ through vascular, natural lumens (e.g., gastroenterological, urinary, or vaginal), percutaneous approaches, through the working channel of laparoscopes, or through the working channel of endoscopes. Further, the catheter may utilize laser energy, mechanical forces, and combination of which to cross a wall of specific organs, vessels, etc., such as to reach a target site. For example, present embodiments may be useful to reach lesion and enable resection of it using non-thermal ablation and mechanical means to cut through a tissue, while inducing minimal collateral damage to the surrounding tissue of the lesions. According to some embodiments, non-thermal, is a term used to define ablation wherein tissue is ablated, usually by a pulsed laser, in manner that tissue is modified or removed without collateral thermal damage due to the nature of interaction of the high-power radiation with tissue and modification of which before absorbed energy is thermally diffusing to the surroundings.

Optionally, the catheter may be utilized for resection of lesions in organs such as the pancreas and liver. The access to the lesions in pancreas can be through the Gastro Intestinal (GI) lumen, such that access through the pancreatic ducts, entering from the common bile duct in an ERCP procedure or through the stomach under EUS guidance. Alternatively, pending on the location of the tumor access through vessels, such as one of the pancreatic arteries, can be an option. In management of tumors in the liver a preferred embodiment can be through percutaneous approach as typically done for percutaneous liver biopsy.

In some embodiments, the objective of the invention is to allow resection and controlled ablation in the periphery in a single path through the lesion. The controlled ablation is performed by emission of radiation to predetermined sections of the surrounding such as a cut of a circle. In some embodiments, the ablation can be performed by microelectrodes surrounding the catheter tip and ablation can be on using electrical power.

The maneuverability of the catheter can be based on human (physician) and/or robotic operation. The control of the ablation can be human and/or computer based. Optionally, the catheter may be operated in conjunction with monitoring means. Monitoring means may be operated prior to, during and/or post operation of the catheter. Non-limiting examples of monitoring means include: spectroscopy, thermal sensing, acoustic monitoring, such as monitoring bubbles/noise, imaging, PET CT, contrast CT, and endoscopic ultrasound (EUS).

Optionally, a control unit may regulate each of: laser wavelength, laser power, and speed of advancement of the catheter according to a signal computed based on imaging/monitoring of the target site/organ.

According to some embodiments, the catheter may be a hybrid catheter, which includes energy means, such as a laser, and mechanical means, such as a blade. Optionally, the catheter may be configured to weaken and/or even cut and detach undesired tissue with a laser and then detaching the rest of the tissue by mechanical means, such as using a blade. The catheter may be further utilized to collect the detached tissue in a form that allows laboratory tests such as pathology, histology and/or other relevant tests. Optionally, the catheter may further be configured to facilitate removal of the extracted tissue (for example, through the longitudinal lumen of the catheter or through another lumen/channel/orifice) such that the extracted tissue may then be collected and sent to a laboratory for further tests such as histology or other types of analysis that can be performed during the procedure to optimize clinical effectiveness and safety by detection of border of tumor, etc., for example, using frozen biopsy.

Optionally, the catheter may further include mechanical means for collection of samples extracted through the lumen of the catheter Operation of the hybrid catheter may be based on a combination of non-thermal laser radiation ablation and mechanical removal of an undesired tissue from a body organ within an advancement path of the catheter. Optionally, the energy means may be configured to further induce thermal necrosis and or non-thermal ablation in an area surrounding the path advancement path of the catheter. This can enable mitigation of risk associated with passing of the catheter through a tumor that can lead to tumor cells spread as is known to be a significant risk in liver biopsy; and/or to increase the cross section of the impact of necrosis beyond the cross-section area of the catheter.

The laser may change the mechanical characteristics of tissue, and thereby improve performance of mechanical tools such as various types of blades or shavers. By way of example, the laser may make a soft tissue crispier so it can be effectively crushed using the mechanical tool. The present catheter, advantageously, provides for controlled ablation of lesions and collection of tissue with minimal collateral damage to surrounding tissues.

Advantageously, usage of the hybrid catheter may result in lesser byproducts than in common laser ablation, lesser associated mechanical stress, and lesser other side effects such as thermal injury resulting from photo ablation. The process may allow using smaller lasers wherein energy is focused at a smaller area and wherein mechanical tools remove traces remaining in the treated area and facilitate further penetration of the laser beam to proceed in effective ablation.

According to some embodiments, the terms "cut", "dissect", "resect", "detach", "debulk" and "remove" may be used here interchangeably.

According to some embodiments, the term "undesired tissue" may refer to any suspected tissue, which needs to be removed and/or further examined.

According to some embodiments, the catheter includes a resection tip, having a first set of optical fibers for front illumination of non-thermal laser radiation which facilitates non-thermal ablation or coagulation of a tissue in front of the catheter, and a second set of optical fibers for side illumination of non-thermal laser radiation which facilitates non-thermal ablation or coagulation of a tissue which is angular or lateral to the catheter, and/or thermal radiation which induces thermal necrosis of a tissue which is angular or lateral to the catheter. Optionally, depth and extent of necrosis and/or coagulation is controlled by laser wavelength, power, and speed of advancement of the catheter. Optionally, the resection tip includes cutting edges.

According to some embodiments, the catheter includes a tip section, which may be essentially in a cylindrical shape, extending along a central longitudinal axis, having: a central longitudinal lumen; a first set of optical fibers operatively coupled to a laser and configured to transmit a laser radiation ('first laser radiation' or 'non-thermal laser radiation') capable of causing non-thermal ablation of target tissue. The laser radiation may be transmitted outside a distal extremity of the tip section in a parallel axis to the central longitudinal axis. The tip section advantageously further includes a second set of optical fibers operatively coupled to a laser and configured to transmit laser radiation ('second laser radiation' or 'non-thermal and/or thermal laser radiation') configured to cause thermal and/or non-thermal ablation of tissue in vicinity to the target tissue of the first laser radiation. According to some embodiments, the extent of ablation and/or damage caused by the second laser radiation may be selectively controlled for example according to the characteristics of the surrounding tissue (e.g. its importance to organ function and/or its sensitivity to thermal damage) Optionally, the tip section further includes a cutter including one or more blades configured to cut a tissue.

The catheter may be further connected to a suction pump that generates low pressure to collect the cut tissue through the catheter, such as through the central longitudinal lumen of the tip section. The pump may be a peristaltic pump connected to a proximal section of the catheter outside a patient's body.

Optionally, a control unit is provided to regulate each of: transmission of non-thermal radiation from the first set of optical fibers, transmission of non-thermal and/or thermal radiation from the second set of optical fibers, and progression of the catheter through the target site according to information computed from monitoring means of the target site.

The term "optical fiber" refers to a wire that can transfer light from one end to other by internal reflection of light within the fiber. An optical fiber may be cladded or non-cladded. Cladded optical fibers generally have a structure from the center to the periphery including core, cladding, and buffer. A non-cladded optical fiber, lacking cladding, generally has an exposed core. The core can be made of any transparent material such as silica (glass) or a polymer that transmits light. In cladded fiber optics, the core is typically surrounded by, but not limited to, a thin plastic or silica cladding that helps transmit light through the optical fiber with minimum loss. The cladding may be covered with a tough resin buffer layer. Both the core and the cladding may be made of dielectric materials such as, but not limited to, doped silica glass and polymers. To confine the optical signal in the core, the refractive index of the core is typically greater than that of the cladding.

Optical fibers of the first set of optical fibers may be configured to distribute radiation distally from a distal extremity of the optical fiber parallel to a central longitudinal axis of the optical fiber's core. In such embodiments, the first set of optical fibers may be circumferentially located along an inner surface of the cylindrical tip section, which is near the periphery or the center of the tip section. Optionally, the first set of optical fibers is embedded within a wall of the tip section and positioned parallel to the central longitudinal axis, such that a laser radiation is transmitted distally from a distal extremity of the tip section parallel to the central longitudinal axis of the tip section.

Alternatively, the circumferentially-directed optical fibers may be located elsewhere but directed, by way of orientation and/or optical focusing, to radiate an area distal to the circumference of the tip section, parallel to the central longitudinal axis of the tip section.

Optical fibers of the second set of optical fibers may be configured to distribute radiation transversely from the optical fiber core. To this end, optical fibers may be modified for transversal distribution for example by way of cutting into or polishing the fiber cladding or chemical polishing or mechanically shaving the clad as in double dads fibers. According to some embodiments, the second set of optical fibers may include 2-16, 4-12, 4-8 optical fibers. Each possibility is a separate embodiment. According to some embodiments, the second set of optical fibers may include at least four optical fibers. According to some embodiments, the optical fibers may be distributed at predetermined circumferential positions around the tip section. As a non-limiting example, the at least four optical fibers may be off-set by a predetermined angle one with respect to the other, e.g., every 90 degrees or every 45 degrees around the tip section.

According to some embodiments, the term "transversely" may refer to any direction, which is not parallel to the central longitudinal axis of the catheter. For example, a direction essentially perpendicular to the central longitudinal axis, or along any axis having an angle of about 10°-170° with the central longitudinal axis.

Figure 2:
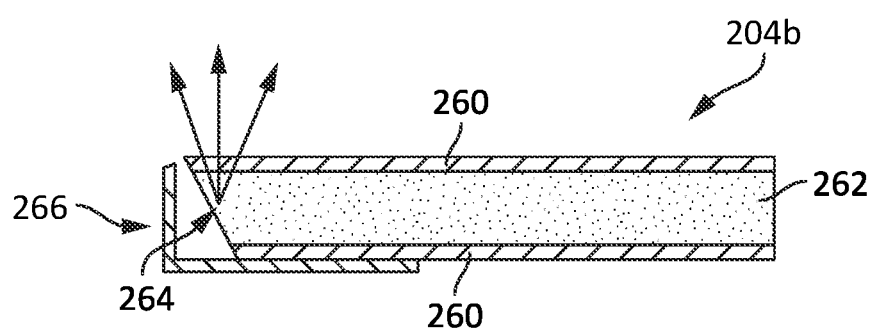
FIG. 2 schematically depicts a modified optical fiber, according to another exemplary embodiment of the current invention.

Non-limiting examples of modified optical fibers for lateral/and or angular illumination are illustrated in FIGS. 1 and 2. FIG. 1 is a side view of a modified optical fiber 104b for lateral/and or angular illumination. Modified optical fiber 104b includes a longitudinal core 160 surrounded by a cladding layer 162. A distal tip 164 of fiber 104b is cut/polished, such as in an angle of about 30 degrees, and a distal portion of cladding layer 162 is removed to expose longitudinal core 160 thereby facilitate side scattering of the light in an angular/lateral direction as indicated by the dashed arrows.

FIG. 2 is a side view of another modified optical fiber 204b for lateral/and or angular illumination. Modified optical fiber 204b is substantially similar to modified optical fiber 104b of FIG. 1 and includes a longitudinal core 260 surrounded by a cladding layer 262. Notably, a distal tip 264 of fiber 204b is cut/polished in a larger angle than the distal portion of fiber 104b of FIG. 1, to trigger internal deletion and folding of the light in 90 degrees indicated by the dashed arrows. Optionally, fiber 204b is further equipped with protection element 266 for protection of distal tip 264 from mechanical damage and/or blockage of forward pointing beams and avoid contact with surface for internal reflection. Optionally, conical fibers (not shown) may be used alone or together with reflecting surface (not shown). Optionally, diffusers (not shown) may be added to increase light divergence or alternatively focusing elements may be used to obtain a more localized interaction. In some embodiments, the polished/cut tip may be coated with reflecting coating to facilitate beam reflection/deflection.

Optionally, the second set of optical fibers may be located along an inner surface of the cylindrical tip section. Optionally, the second set of optical fibers is embedded within a wall of the tip section positioned parallel to the central longitudinal axis and proximally to the distal extremity of the tip section, such that a laser radiation is transmitted distally from a distal extremity of the tip section transversely to the central longitudinal axis of the tip section. Additionally, or alternatively, the laser radiation may be transmitted through the wall of the tip-section (proximally to its distal end opening), for example through optical windows formed in the wall.

Optionally, the first set of optical fibers and the second set of optical fibers may be co-embedded within a wall of the tip section.

Optionally, the cutter is a circular action cutter. The circular action cutter is positioned outside optical paths of the first and the second laser radiation. The circular-action cutter may be located in a central part of the tip section, for example, surrounded by the first set and the second set of optical fibers.

Alternatively, the circular-action cutter may be located in the periphery of the tip section and the first set of optical fibers may be located in a central part of the tip section, for example, surrounded by blades. In a non-limiting example a first circular cutter is located in a central part of the distal extremity of the tip section surrounded by the first set of optical fibers, and a second circular cutter is located at the periphery of the distal extremity of the tip section while the second set of optical fibers are located at the periphery of the tip section, proximal to the distal extremity thereof.

According to some embodiments, at least one of: the one or more blades and the first and the second sets of optical fibers are located in the periphery of the tip section. According to some embodiments, the one or more blades and at least one of the first and second sets of optical fibers are located in the periphery of the tip section. According to some embodiments, the first and the second sets of optical fibers and the one or more blades are located in the periphery of the tip section.

According to some embodiments, the first set of optical fibers, the second set of optical fibers, and the one or more blades are located in a central part of the tip section. According to some embodiments, at least one of: the first set of optical fibers, the second set of optical fibers, and the one or more blades are located in a central part of the tip section. According to some embodiments, the one or more blades and at least one of: the first set of optical fibers and the second set of optical fibers, are located in a central part of the tip section.

According to some embodiments, the circular-action cutter lays on a spring so that a maximum force applied by the cutter is predetermined in order to avoid potential damage yet be effective. The tip section may include an inner channel maintained at a relative low pressure to suck the undesired material (e.g., tumor tissue).

Optionally, a motor is provided to rotate the circular-action cutter in order to improve fragment cutting and/or detaching. Additionally, or alternatively, the motor or a different motor may be used to rapidly vibrate the circular-action cutter in order to improve fragment cutting and/or detaching. Optionally, the circular-action cutter is heated to improve its performance. This may be done by an external heat source, electrical means and/or by the laser radiation.

According to some embodiments, the catheter tip may be expandable, such that its diameter may be increased after its introduction in a target site. According to some embodiments, the catheter tip may include means for deflection, such that effective working area will be larger than the catheter diameter and enable off-axis work.

Optionally, each of the first set of optical fibers and the second set of optical fibers is independently operatively linked to a laser. The first set of optical fibers and the second set of optical fibers may be operatively linked to different types of lasers and/or to the same type of laser. Optionally, a high power pulsed laser may be utilized for non-thermal ablation or coagulation and a continuous-wave (CW) laser is utilized for induction of thermal necrosis. Examples of lasers use to induce thermal necrosis include Nd:YAG, green laser, 980 nm, thulium and holmium lasers. According to some embodiments, the laser functionally connected to the second set of optical fibers may be a multifunctional laser, i.e., a laser capable of transmitting laser radiation at different wavelength, intensities and/or pulses. The multifunctional laser thus enables transmitting laser radiation in a selectively controlled manner e.g., according to a selection mode selected by a user and/or according to an operation mode automatically determined for example based on images of the target tissue received prior to the treatment. According to some embodiments, the second set of optical fibers may be connected to a laser diode capable of transmitting a predetermined laser radiation. According to some embodiments, the second set of optical fibers may be connected to more than one laser diode, each diode capable of transmitting a predetermined laser radiation. Such configuration enable transmitting laser radiation in a selectively controlled manner based on the selective activation of certain of the more than one laser diodes. The activation may be determined by a user and/or be to automatically determined for example based on images of the target tissue received prior to the treatment.

A laser beam for non-thermal ablation may be directed through fibers each having a core diameter optionally in the range of 40-250 microns. In a configuration where the catheter's circumference is, for example, 2 mm, using fibers at two circles at the periphery of the catheter with an outer diameter of 70 microns will result in using approximately 110 fibers with a cross-section area smaller than 1 $mm^2$, so that for a coupling efficiency of 50%, the energy at the exit of each fiber will be close to 40 mJ/mm when pumped with a 80 mJ laser. Adequate fibers for some embodiments may be all-silica fibers with a pure silica core. These fibers can usually withstand more than 5 $J/cm^2$ in the input. Some embodiments include fibers with a numerical aperture (NA) in the range of 0.12-0.22. An example of a relevant fiber is FiberTech Optica's SUV100/110AN fiber for UV application and the low OH version SIR100/140AN for use with laser in the 1900-2100 nm range or Infrared Fiber Systems, IR Photonics and A.R.T. Photonics GmbH fibers for transmission of radiation in the 2900-3000 range. Embodiments of single mode or multimode may be realized while preservation of beam quality is important but not mandatory in certain embodiments. Some embodiments may include micro-lenses at the tip area to manipulate the beam at each individual fiber exit. The power required for effective ablation with 355 nm, 10 nsec pulses (approximately 30-60 mJ/mm$^2$) is close to the damage threshold of certain fibers or above it, which lead, in existing products, to the need of extended pulse length, for example. According to some embodiments, high peak power is maintained and accordingly the catheter may include means for delivery of the laser power through relatively bigger optical fibers, e.g., 100 or even 300 micron fibers that do not extend all the way to the end of the tip section.

An example of an appropriate laser of some embodiments is a solid state ultraviolet (UV) laser emitting pulses in approximately 355 nm and/or 266 nm. An example of an appropriate laser is solid state Nd:YaG laser, emitting 50 mJ, 10 ns pulses of 355 nm at 50 Hz and/or 40 mJ of 266 nm at 40 Hz. Another example is an Excimer laser. Other examples of laser for non-thermal ablation include pulsed laser with wavelengths around the water absorption in 1.9-2 microns or 2.9 microns.

In case of using significantly high repetition rates, thermal effects in the tissue may become a problem. This can be at least partially resolved by minimizing ablation area (depth and width), use of short laser pulses and with saline flushing. Another option includes sequential illumination of fibers in a manner that not all the fibers are exposed to laser ration simultaneously, in order to enable thermal relaxation of the affected tissue.

In an embodiment, dyes or substrates may be used to enhance absorption at certain wavelengths, such as 355 nm. For example, sensitization with haematoporphrin or tetracycline prior to the procedure, in order to enhance ablation of the pretreated atheromatous plaque but not insensitised or normal arterial wall.

Another example of a laser of some embodiments is a laser emitting pulsed radiation in the mid-infrared (IR) region, such as in the range of 2.8-3 micrometers, a range where water is very effectively absorbed. Additionally, or alternatively, radiation at around 2 microns may be used, with a preference for thulium laser emitting at 1910-1940 nm range wherein there is higher absorption of water preferably combined with Q-switched modulation wherein ablation is more effective and reduces collateral damage. For 3 micron emission, an Er:YAG may be used, or another source such as a Mid-IR Holmium Fiber Laser Directly Pumped with Diode Laser that emits at 2840 nm using fluoride fibers [see Optics Letters, Sep. 1, 2007, pp. 2496-2498].

Yet another example is usage of a third harmonic of a Nd:YAG laser at 355 nm, preferably a compact, all solid state, diode pumped laser. The 355 nm radiation usually has a deeper penetration capability compared to the 308 nm radiation, in the depth range of 100 micron or more in relevant tissues and materials. Optionally, very short pulse widths (such as <10 ns) are used, in order to obtain a higher power density, and, in particular, to be able to ablate hard tissue. In accordance with some embodiments, the energy per pulse is in the range of 10-100 mJ and the pulse frequency is in the range of 10-100 Hz. Optionally, the area of ablation may be flushed with a saline solution in order to reduce side effects (such as cavitation), clean the area of ablation and catheter and/or facilitate collection of debris.

One of the advantages of using 355 nm radiation is that is considered relatively non-mutagenic. The 308 nm radiation of the xenon chloride laser is in the UVB range, which is known to have mutagenic risks. [Walter Alexander. Journal of Clinical Laser Medicine & Surgery. AUGUST 1991, 9(4): 238-241. doi:10.1089/clm.1991.9.238.]

Some prior studies have indicated that third harmonic lasers are generally less suitable for tissue ablation than 308 nm lasers, due to longer penetration rates and reduced effectiveness of ablation (see, for example, Grundfest W S et al., Am J. Surg. 1985 August; 150(2):220-6; and Frank Laidback et al., Lasers in Surgery and Medicine 8:60-65 (1988)). The present embodiments, however, may successfully utilize third harmonic Nd:YAG lasers instead of complex and expensive Excimer lasers. This may for example be achieved using a hybrid catheter in which the laser and the mechanical cutter share the task of tissue resection; the laser may ablate and/or weaken at least some of the material, while the mechanical cutter completes the job by finally detaching the material. According to some embodiments, the cutter may have a sharpness configured to prevent or minimize cutting of non-ablated tissue.

In some embodiments, a laser that emits radiation in 266 nm may be used. This wavelength has a shorter penetration rate in addition use of compact Excimer laser emitting radiation at 308 nm, as currently used, can be utilized with the current embodiments According to some embodiments, a system may include means that enable an operator to switch between 266 nm and 355 nm, generated from the same Nd:YAG laser, and means to control power, repetition rate and/or exposure/illumination of specific fiber groups.

An alternative embodiment of the present invention replaces UV lasers with a laser with radiation in the 2 micron or 2.8-3 microns, in which ablation is very effective.

Holmium lasers are conventionally used for 2 microns but Thulium lasers have a stronger water absorption and smaller absorption length, which makes them especially suitable for some embodiments. For example, in an embodiment, pulsed fiber thulium laser is used. Alternatively, a solid-state laser may be used in order to increase pulse power per pulse, which is currently limited in fiber lasers and in view of the limited pulse rate that can be used in order to minimize heataccumulation and damage.

Laser in 2.8-3 micrometer may be Er:YAG. Er:YAG Q-switched are available with pulses in the hundreds of nanosecond range, which may be suitable for present embodiments. See, for example, M. Skorczakowski, et al, Laser Physics Letters Volume 7, Issue 7, pages 498-504, July 2010. Another laser example which may be suitable for specific embodiments is Pantec's model DPM-15 solid state laser, emitting microsecond pulses in the mJ range at hundreds of KHz.

In an embodiment, fiber lasers which may be directly diode-pumped, such as a Mid-IR Holmium Fiber Laser, are used. This laser may be pumped from ground level ($^5I_8$) to an excited energy band ($^5I_6$) with radiation at about 1150 nm, and the relaxation bands may lead to emission at 2840 nm (relaxation to band $^5I_7$) and 2100 nm in relaxation to ground state.

Accordingly, this laser may be directly pumped with recently developed high-power, high-brightness diode lasers based on highly strained InGaAs quantum wells that produce output at 1148 nm. See Optics Letters, Sep. 1, 2007, pp. 2496-2498 and Stuart D. Jackson Optics Letters, Vol. 34, Issue 15, pp. 23272329 (2009).

The laser may be selected according to the selected resonator optics, for example fluoride fiber lasers to emit laser radiation on the 2.9-μm transition (516 to 517) and silica fiber lasers to emit radiation on the 2.1-μm transitions (517 to 518). An advantage of an embodiment using a laser in the region of 2.9-3 micron is that the absorption is very high and results in very short length of absorption, in the order of 15 microns only. Therefore, the relaxation time is shorter so the pulse rate may be increased to above 100 Hz in order to accelerate the procedure.

Throughout the following description, similar elements of different embodiments of the device are referenced by element numbers differing by integer multiples of 100. For example, a cylindrical tip section of FIG. 3 is referenced by the number 300, and a cylindrical tip section of FIG. 4, which corresponds to cylindrical tip section 300 of FIG. 3, is referenced by the number 400.

Figure 3A:
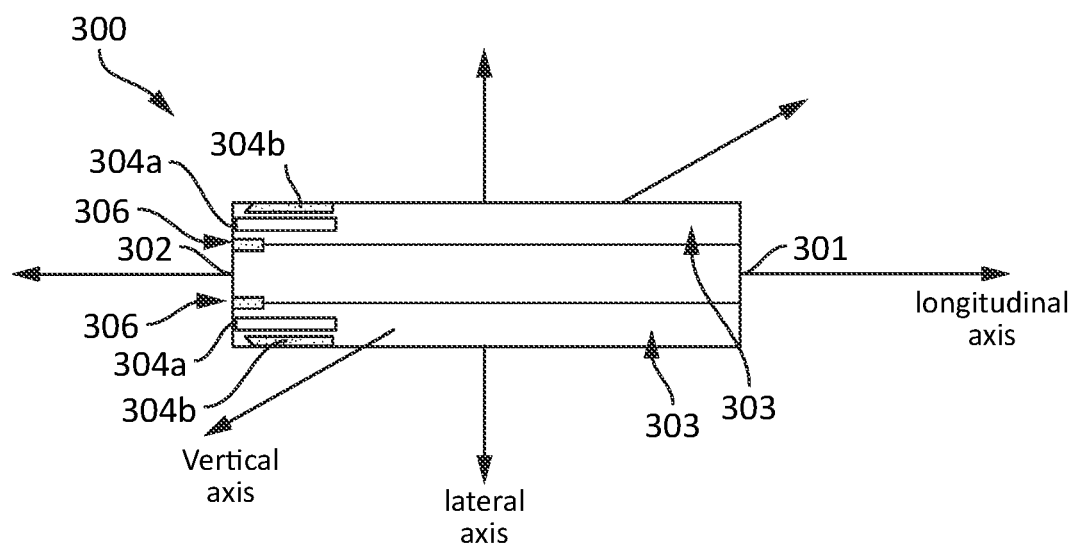
FIG. 3A is a cross section side view of a cylindrical tip section of a catheter, according to an exemplary embodiment of the current invention.

Reference is now made to FIGS. 3A, 3B and 3C, which show an exemplary cylindrical tip section 300 of a catheter in a perspective (FIG. 3A) and front (FIGS. 3B and 3C) views, in accordance with an exemplary embodiment. The remainder of the catheter's shaft (not shown) may, in some embodiments, be biocompatible polymer tubing, optionally coated, to minimize friction with the body's organs.

To facilitate the description of cylindrical tip section 300, three orthogonal axes are indicated in FIG. 3A. The axis labelled 'longitudinal axis' refers to a central axis that runs along a length of cylindrical tip section 300, from a proximal end 301 to a distal end 302. The axis labelled 'lateral axis' indicates the width of sleeve cylindrical tip section 300. The axis labelled 'vertical axis' is perpendicular to both the lateral and the longitudinal axes.

Cylindrical tip section 300 may include a cylindrical housing 303, a first set of optical fibers 304*a* that transmit light/laser beams outside cylindrical tip section 300 parallel to the longitudinal axis, a set of modified optical fibers 304*b* ('second set of optical fibers') that reflect/deflect light/laser beams outside cylindrical tip section 300 transversely to the longitudinal axis and a cutter 306 positioned inwardly of first and second sets of optical fibers 304*a* and 304*b*, respectively. Alternatively, in an embodiment (not shown), the cutter may be positioned outwardly of at least one of first and second sets of optical fibers 304*a* and 304*b*, respectively. It is intended that the following description of the embodiments in which the cutter is positioned inwardly, be applied, mutatis mutandis, to the alternative, not-shown embodiment.

Cutter 306 is optionally an annular blade (not shown) extending to a certain depth inside tip section 300. Optionally cutter 306 may be coupled to a suitable motor (not shown), located in tip section 300 or further in the shaft, supplying rotary and/or vibratory power to the blade of cutter 306. Optionally, one or more flexible members (not shown), such as a spring, may interact with cutter 306 at its proximal base, to allow it to retract and protrude distally from housing 302. The annular blade of cutter 306 may have sufficiently thin edges, such as around 100 microns. Suitable blades may be tailor-made by companies such as MDC Doctor Blades, Crescent and UKAM. The blade may optionally be mounted at the end of a rotatable tube rotated. Such tubes are available from manufacturers such as Pilling, offering a line of laser instrumentation and blade manufacture. The blade may be metal or manufactured by molding a material such as plastic which is optionally coated with a coating having proper characteristics for in-vivo use.

An exemplary tip section may have an external diameter of approximately 5 mm, an internal diameter (within the innermost layer, be it the cutter or an extra wall) of approximately 3.4 mm, and optical fibers each having an approximately 0.1-0.2 mm diameter.

Optionally, each of first set of optical fibers 304*a* and second set of optical fibers 304*b* are positioned along an inner surface of housing 303 of cylindrical tip section 300. Second set of optical fibers 304*b* may be positioned outwardly to first set of optical fibers 304*a*. Optionally, set of modified optical fibers 304*b* is assembled in the periphery of the catheter and the fibers are processed at the distal end to enable side illumination. Optionally, set of modified optical fibers 304*b* is wrapped around the distal tip to point to the side. In such embodiments, high numerical aperture (NA) such as 50 micron fiber may be used to minimize undesired leakage.

Each of optical fibers 304*a* and optical fibers 304*b* may be independently connected, at their proximal end (not shown) to one or more laser sources (not shown) characterized by one or more of the parameters laid out above. Optical fibers 304*a* may deliver the laser beams from the source towards the intervention site in the body parallel to the longitudinal axis of the cylindrical tip section 300. Optical fibers 304*b* may deliver the laser beams from the source towards the intervention site in the body transversely to the longitudinal axis of the cylindrical tip section 300.

Referring to FIGS. 3B and 3C, to address the heterogeneity of the tissue and need to control necrosis to avoid damage to blood vessels, ducts and healthy tissue, different doses of radiation and type of radiation can be transmitted, by controlling the wavelength, intensity and or pulse of the laser radiation to the appropriate fiber or groups of fibers.

FIG. 3B, is a front view of cylindrical tip section 300 showing three modified optical fibers 304*b*, indicated as 304*b*-1, 304*b*-2, and 304*b*-3, embedded within to housing 303. Each of modified optical fibers 304*b*-1 304*b*-2, and 304*b*-3 transmits radiation, indicated by dashed arrows, at a wavelength and a dose required to obtain a desired impact. Optical fiber 304*b*-1 transmits radiation in a specified wavelength and dose which results in thermal ablation/necrosis of an area 311 transversely to the longitudinal axis of the cylindrical tip section 300.

FIG. 3C is a front view that illustrates transmission of different laser wavelengths by optical fibers 304*b*, indicated herein as optical fiber 304*b*-4, optical fiber 304*b*-5, optical fiber 304*b*-6 and optical fiber 304*b*-7, for different type and/or depth of interactions. For a large thermal impact such as in area 312 a thermal radiation is transmitted by optical fiber 304*b*-4. In a non-limiting example, a CW laser such as in 980 nm can be used with large penetration that generate a large thermal impact. In another example, a 1060 CW or O switch laser can be used. For a more controlled impact such as illustrated in area 313 optical fiber 304*b*-5 may transmit radiation from a laser in 535 nm for example and O-switch can be used to decrease thermal damage. Also, the control of repetition rate and/or power and/or exposure time (for example through control of catheter advancement) can impact the extent thermal damage. Optical fiber 304*b*-6 transmits radiation which results in a very superficial impact as illustrated in area 314. To this end the dose of exposure may be controlled and/or a laser such as O-switched 355 nm that is used for resection in some embodiments, may be used. Alternative embodiments use laser with high absorption of water such as Er:YAG or Thulium. As illustrated in FIG. 3C a vessel 315 passes at the left of the catheter, therefore optical fiber 304*b*-7 that is in very close proximity to the vessel is not utilized until the catheter passes the vessel.

In some embodiments, the catheter is used to perforate the access lumen, organ such as the stomach, pancreas ducts or vessels that access the liver or pancreas. In a first mode of operation using high power pulses laser combined with a blunt blade that enables perforation, achieved in some embodiments by increase of laser power above a certain threshold such as >50 mJ/mm2 in 1 Onsec pulses of 355 nm, and when the targeted organ is reached the mode of work is changed. In some embodiments, the laser power is reduced to powers density in the range of 30-50 mJ until it gets to the lesion that needs to be respected and then accompanied by thermal and/or no thermal ablation when addition of side fired laser beams is added. In some embodiments, diode can replace the laser beam, in some embodiments direct or secondary means for thermal conductance are added. The thermal element can be based on metal components that are heated by laser light or electrical power.

In some embodiments, side/lateral impact is induced by PDT and in some is embodiments the catheter can be used to deliver synthesized dyes.

In some embodiments, a small array of small electrodes is assembled at the periphery of the catheter tip to induce localized thermal impact between at least a pair of electrodes. In some embodiments, the electrodes can be coupled to a RF stimulators with a multiplexer that controllers which electrodes are activated at a certain time point per location and required area to be ablated.

In some embodiments, at least one US transducer is assembled to enable on-line monitoring.

Alternatively, in an embodiment (not shown), the tip section does not include any cutter.

Figure 4A:
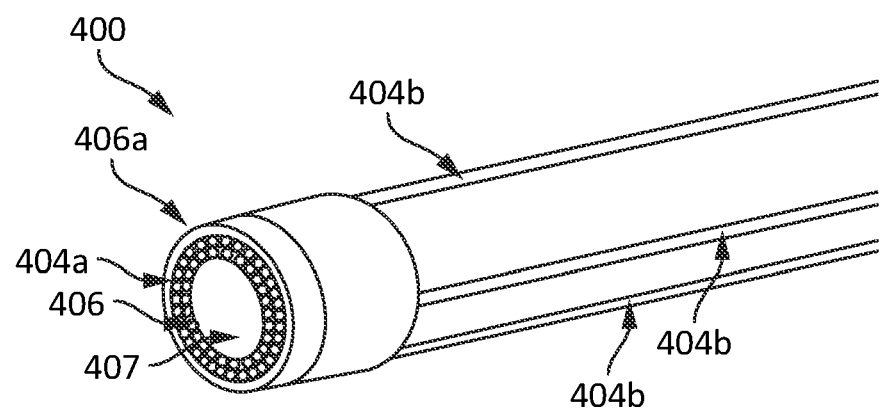
FIG. 4A is a perspective view a cylindrical tip section of a catheter, according to an exemplary embodiment of the current invention.
Figure 4B:
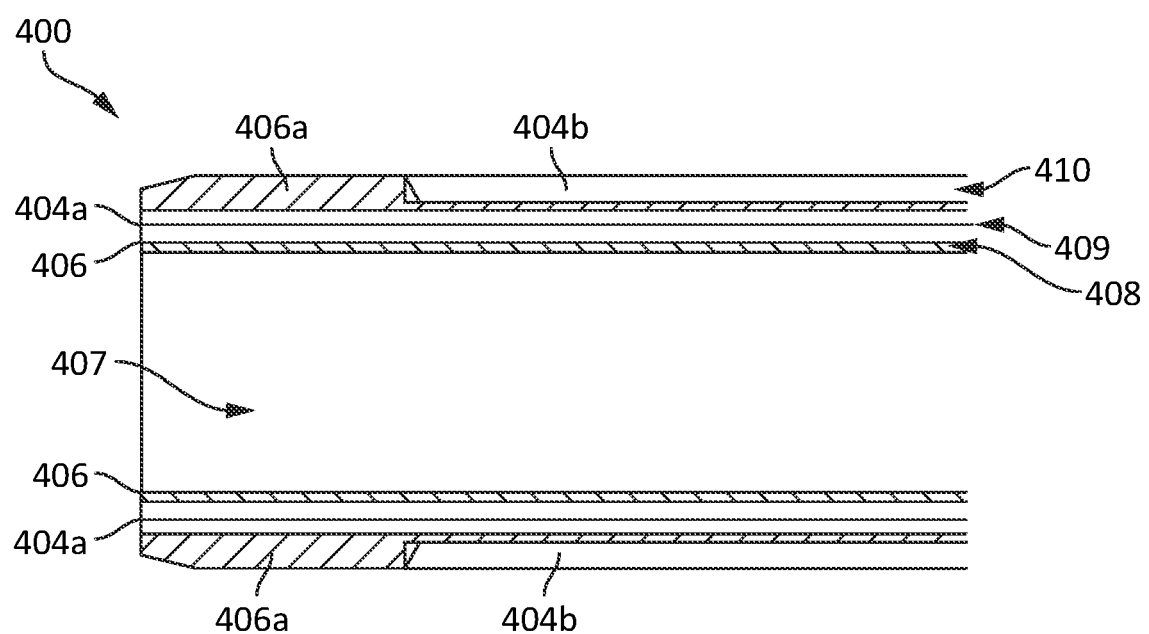
FIG. 4B is a cross section side view of the cylindrical tip section of FIG. 4A, according to an exemplary embodiment of the current invention.
Figure 4C:
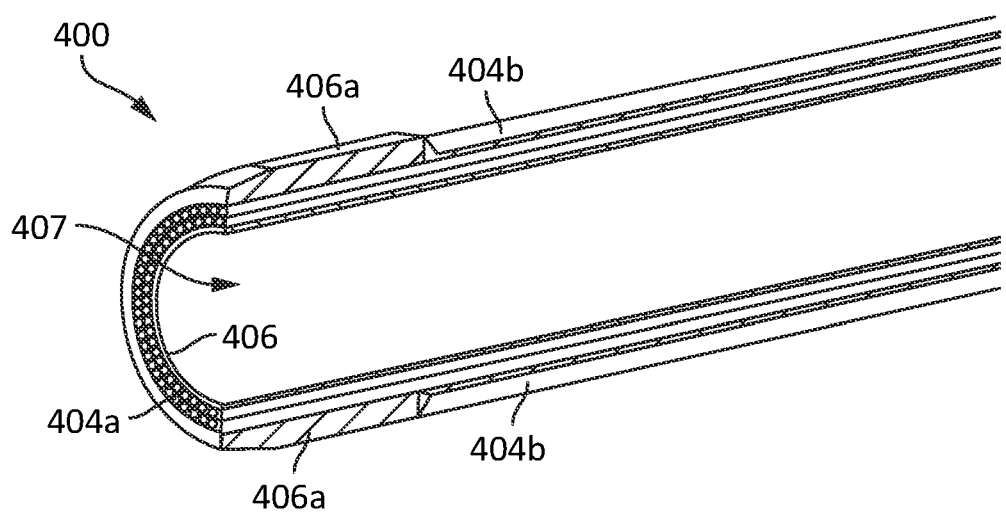
FIG. 4C is a cross section view of the cylindrical tip section of FIG. 4A, according to an exemplary embodiment of the current invention.

Reference is now made to FIGS. 4A, 4B, and 4C which show an exemplary cylindrical tip section 400 of a catheter, in a fully assembled view, a cross sectional side view, and a cross section perspective view, respectively, in accordance with an exemplary embodiment. Cylindrical tip section 400 may be similar to tip section 300 of FIGS. 3A-C with some alterations. Similarly, to cylindrical tip section 300 of FIGS. 3A-C, cylindrical tip section 400 may include a first set of optical fibers 404a that transmits light/laser beams outside cylindrical tip section 400 parallel to the longitudinal axis, a set of modified optical fibers 404b (second set of optical fibers') that reflect/deflect light/laser beams outside cylindrical tip section 400 transversely to the longitudinal axis and a cutter 406. Notably, a second cutter 406a may be positioned circumferentially to tip section 400 and distally to a set of modified optical fibers 304b. Further, tip section 400 may include a collection channel 407 which extends along its longitudinal axis and extending outside the body. Optionally, a suction element (not shown) is applied from outside the body in order to evacuate the collected tissue which was treated by the lasers and/or cutter 406.

Optionally, cutter 406 is delimited and/or supported by a first inner to wall 408. Optionally, first set of optical fibers 404a are delimited and/or supported by a second inner wall 409. Further, second set of optical fibers 404b are delimited and/or supported by a third wall 410 proximally to second cutter 406a.

Alternatively, in an embodiment (not shown) the tip section does not include any cutter.

Figure 5:
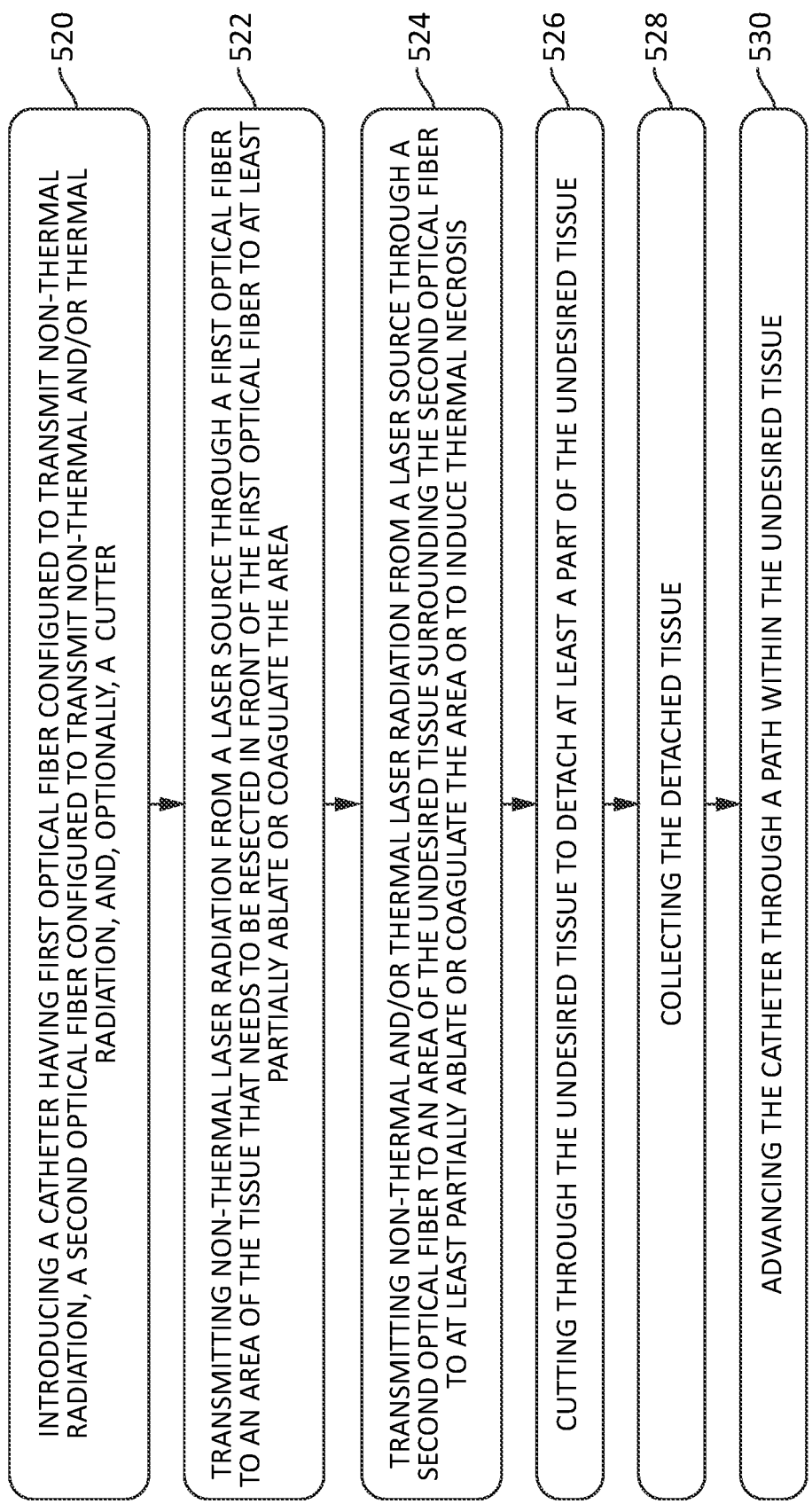
FIG. 5 is a flowchart of the steps of a method for resecting and/or ablating an undesired tissue, according to an exemplary embodiment of the current invention.
Figure 6A:
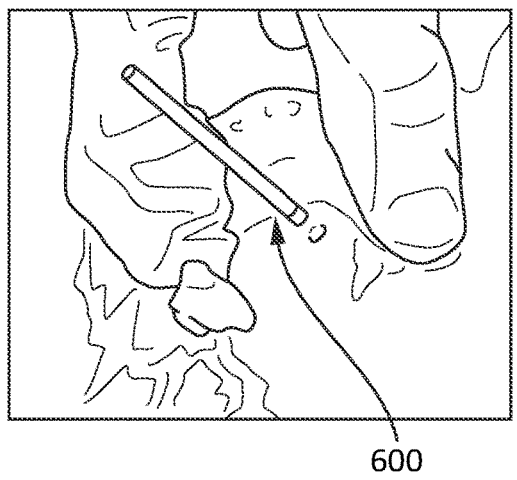
FIGS. 6A-B are photographs illustrating resection of lesions from porcine pancreas using a catheter without collateral thermal damage, according to an exemplary embodiment of the current invention.
Figure 6B:
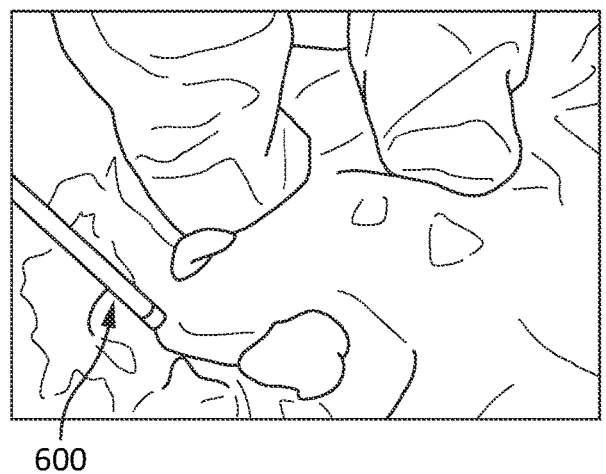
Figure 6C:
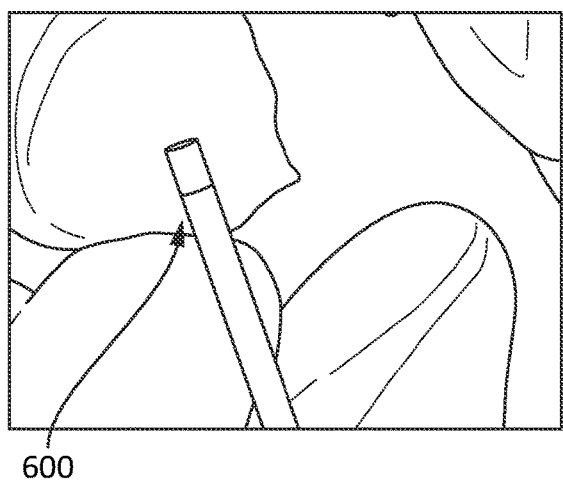
FIG. 6C is a photograph illustrating a tissue extracted mechanically using the catheter of FIGS. 6A and 6B, according to an exemplary embodiment of the current invention.
Figure 6D:
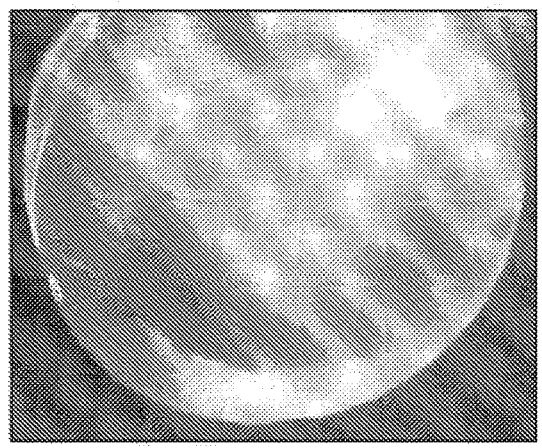
FIG. 6D is a photograph illustrating a tissue extracted by vacuum using the catheter of FIGS. 6A and 6B, according to an exemplary embodiment of the current invention.

Reference is now made to FIG. 5, which is a flow chart of a method for resection and ablation or coagulation of undesired tissue from a body organ, for example, in accordance with a catheter such as disclosed in the system of FIG. 3A-C or 4A-C.

A catheter having first optical fiber (or set of optical fibers) configured to transmit non-thermal radiation, a second optical fiber (or set of optical fibers) configured to transmit non-thermal and/or thermal radiation, and optionally, a cutter is introduced into a target site which includes an undesired tissue (step 520). Optionally, the undesired tissue is a tumors or lesions within a body organ.

A non-thermal laser radiation is transmitted from a laser source through the first optical fiber to an area the tissue that needs to be resected in front of the first optical fiber to at least partially ablate or coagulate the area (step 522). Optionally, the first optical fiber transmits laser radiation from a distal edge thereof in a direction parallel to a central longitudinal axis thereof.

A laser radiation is transmitted from a laser source through the second optical fibers to an area of the undesired tissue surrounding the second optical fiber to at least partially ablate or coagulate the area or to induce thermal necrosis (step 524). Optionally, the second optical fiber is modified to transmit laser radiation from a distal edge in an angular direction to a central longitudinal axis thereof. According to some embodiments, several (for example, different) wavelengths and power levels may be used for each of the fibers of the second fiber set, in different directions or the same direction depending on the 3D shape and material of the lesion.

The undesired tissue is cut through to detach at least a part of the undesired tissue (step 526). Optionally, the cutting is performed by an annular cutter.

Advantageously, the non-thermal ablation of the undesired tissue (e.g. tumor tissue) allows its resection in such manner that samples may be taken for biopsy. Therefore, the method may optionally, further include collecting the detached tissue for example for biopsy (step 528).

Optionally, the catheter is advanced through a path within or in proximity to the undesired tissue (step 530).

Each of Steps 522, 524, 526, 528 and 530 may be performed simultaneously, sequentially, or intermittently. Additionally, or alternatively, each of steps 522, 524, 526, 528 and 530 may be performed in an interchangeable order. Further, each of Steps 522, 524, 526, 528 and 530 may be performed repeatedly.

Reference is now made to FIGS. 6A, 6B, 6C, and 6D which illustrate a method for resection of lesions in a porcine pancreas with a 6 F (2 mm) catheter which includes cylindrical catheter tip 600 which is substantially similar to cylindrical catheter tip 400 of FIGS. 4A-C. In some embodiments catheter tip 600 may be maneuvered to access specific sites. The catheter can be inserted through vessels or ducts or through the stomach in endoluminal procedures or as part of laparoscopy and surgery procedures. The catheter can be used to cross the wall of specific organs, vessels, etc. and get to the target by use of laser energy, mechanical forces, and combination of which. The perforation can be obtained in several embodiments by increase of laser power such as use of >40 mJ/mm2 of 355 nm Q Switched laser. In some embodiments, it is combined with resection of tissue at the center for histology.

Optionally, the catheter includes additional means for ablation of tissue that surrounds the path the catheter passes through. This can enable mitigation of risk associated with passing of the catheter through a tumor that can lead to tumor cells spread as is known to be a significant risk in liver biopsy; and/or to increase the cross section of the impact of necrosis beyond the cross-section area of the catheter.

In some embodiment, coagulation and/or necrosis of tissue surrounding the path the catheter passes is induced by using laser ablation and/or mechanical cutting while combining side illumination to trigger side impact in a distance of 0.1-10 mm from catheter wall (=>overall impact length of 2.2-20 mm, when using a 2 mm in diameter catheter) pending on power and wavelength (in some embodiments pulse laser maybe used), without a need for multiple catheter insertions and/or puncturing to deal with tumors that are larger than the cross section of the catheter.

Optionally, a side impact may be controlled by adding to the 2 mm in diameter catheter, 1-12 side illuminating fibers, at the catheter tip, that emit radiation that ablates and/or coagulates the tissue at a length that is determined by wavelength: for example 1-5 mm with 1550 nm laser, 1-10 mm with 980/1064 nm, 0.5-2 mm=with 532 and sum millimeter using UV light as the 355 nm. These fibers can be part of the ablating fibers for resection and the covering shrink can be transparent to those wavelengths, or the fibers may be exposed without shrink coverage or covered with transparent cover as a fused silica tube. In some embodiments, some of the circular illumination fibers are modified for side illumination by angle polishing, chemical etching and/or splicing. In some embodiments, a prism is used to deflect the emitted light from the fiber to the side. In some embodiments diffraction/deflection gratings are used, in some embodiments the grating can be embedded at the fiber output end. In some embodiments, the grating can be placed proximal to the distal end of the catheter.

In some embodiments, a circular side illumination is obtained with a ring illumination at the tip.

According to some alternative embodiments, the method may include utilizing a hybrid catheter including the first set of optical fibers configured to cause non-thermal ablation of target tissue and a cutter configured to assist in the resection of the tissue while being devoid of a second set of fibers i.e. without transmitting laser radiation to an area surrounding the undesired tissue so as to cause thermal and/or non-thermal ablation thereof. The combined action of the optical fibers and the cutter ensure controlled resection of undesired tissue while avoiding potentially harmful damage to surrounding tissue. According to some embodiments, the method may include "slice-wise" resection of the undesired tissue (e.g. the tumor) by repeated insertion of the catheter into different areas thereof.

Figure 7A:
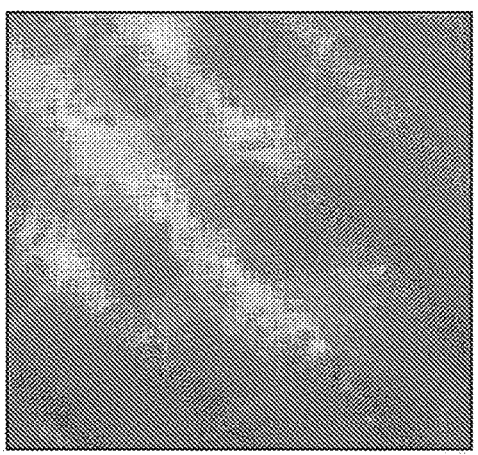
FIGS. 7A and 7B are a microscopic photograph and a photograph, respectively, of necrotic pancreas tissue induced by a combination of laser resection and thermal necrosis, according to an exemplary embodiment of the current invention.
Figure 7B:
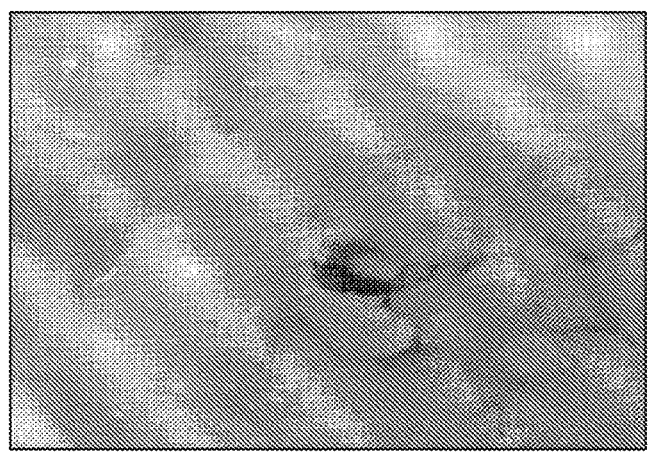

Reference is now made to FIGS. 7A and 7B which illustrate necrosis of pancreatic tissue by combination of laser resection and thermal necrosis. In some embodiments circular illumination and impact with radial symmetry is adequate from clinical consideration, but in others a more localized controlled is required, for example when there is a need to deal with tumors without radial symmetry and/or when close to sensitive structures such as blood vessels, nerves, etc., or when tissue is not homogenous and different energy doses are required as different areas and/or need to deal with the known heat sink effect that may modulate impact of energy dose response. As the lesions are 3D in nature, and the organ characteristics in different plans varies, in many of the relevant cases, the symmetry may change as the catheter passes through the tumor.

Figure 8:
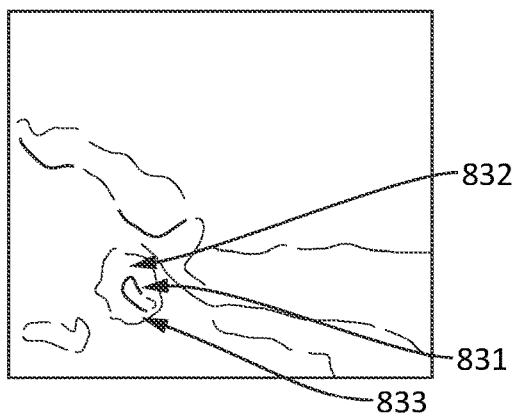
FIG. 8 is a photograph illustrating a porcine pancreas tissue which include areas that were treated by non-thermal radiation and areas that were treated by thermal radiation, according to an exemplary embodiment of the current invention.

Reference is now made to FIG. 8 showing an example that combine resection without thermal damage and induced necrosis in a porcine pancreas by thermal ablation. An area of resected tissue 831 is seen together with an area of necrosis 832 which was induced by non-radial symmetrical illumination while the illumination fiber passes through the organ wherein a 3 Watts 980 nm CW laser is used. In other areas that are not illuminated no necrosis is seen 833.

In some embodiments, the physician or robot may rotate or vibrate the catheter while it moves forward to assure there are no "no-kill" zones at the periphery of the necrosis induced by specific fibers. This can be specifically important when side ablation is triggered by short pulses and wherein ablation is less of a thermal characteristic and therefore interaction is limited to areas directly affected by laser and less spread through to thermal diffusion. Example of such ablation effects can be when Q Switched laser light is used.

Figure 9:
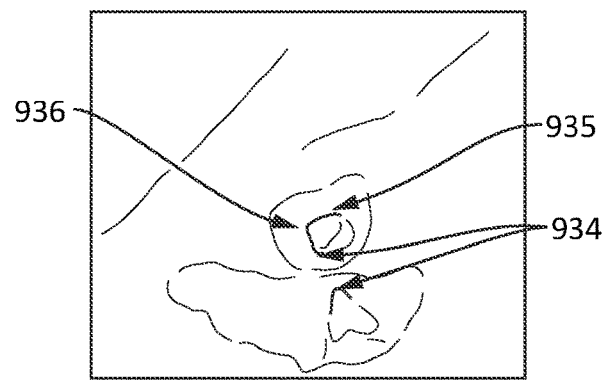
FIG. 9 is a photograph of a section of chicken breast illustrating areas that were treated by non-thermal radiation and areas that were treated by thermal radiation.

By controlling the laser wavelength, power and movement speed the characteristic of the interaction with tissue from no interaction to delicate coagulation to carbonization can be controlled. This is illustrated in FIG. 9, which is a cut from a chicken breast wherein areas of carbonization 934 are shown together with areas of no interaction 935 to coagulation 936, using a 2 watts CW 1550 nm laser. In other embodiments, not shown also non-thermal ablation using pulsed laser and/or a combination of thermal and non-thermal ablation may be used.

While a number of exemplary aspects and embodiments have been discussed above, those of skill in the art will recognize certain modifications, permutations, additions, and sub-combinations thereof. It is therefore intended that the following appended claims and claims hereafter introduced be interpreted to include all such modifications, permutations, additions, and sub-combinations as are within their true spirit and scope.

In the description and claims of the application, each of the words "comprise" "include" and "have", and forms thereof, are not necessarily limited to members in a list with which the words may be associated.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments unless the embodiment is inoperative without those elements. Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

The flowcharts and block diagrams in the Figures illustrate the architecture, functionality, and operation of possible implementations of systems, methods, and computer program products according to various embodiments of the present invention. In this regard, each block in the flowcharts or block diagrams may represent a module, segment, or portion of instructions, which comprises one or more executable instructions for implementing the specified logical function(s). In some alternative implementations, the functions noted in is the block may occur in a different order than the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or act or carry out combinations of special purpose hardware and computer instructions.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent, or patent application was specifically and individually indicated to be incorporated herein by reference. In addition, citation, or identification of any reference in this application shall not be construed as an admission that such reference is available as prior art to the present invention.

What we claim is:

1. A catheter comprising:
   a distal end, a proximal end, and a central longitudinal axis;
   a first set of optical fibers positioned about the central longitudinal axis between the distal end and the proximal end, wherein the first set of optical fibers are configured to transmit laser radiation in a first direction substantially transverse to the central longitudinal axis;
   a cutter configured to cut an undesired tissue, the cutter having a distal end and a proximal end, wherein the proximal end of the cutter is positioned distally of the first set of optical fibers; and
   a central longitudinal lumen configured to collect the cut undesired tissue therethrough upon application of low pressure generated therein.

2. The catheter of claim 1, wherein the cutter is positioned circumferentially about the distal end of the catheter.

3. The catheter of claim 1, further comprising:
   a second set of optical fibers positioned about the central longitudinal axis and configured to transmit laser radiation in a second direction substantially parallel to the central longitudinal axis.

4. The catheter of claim 3, wherein the cutter is positioned at least partially circumferentially inwardly or outwardly of the second set of optical fibers.

5. The catheter of claim 4, wherein laser radiation from the second set of optical fibers is configured to resect and/or ablate the undesired tissue located distally of the second set of optical fibers.

6. The catheter of claim 3, wherein the first set of optical fibers and the second set of optical fibers are independently and selectively operable.

7. The catheter of claim 3, wherein the first set of optical fibers is operatively coupled to a first laser and/or a first laser diode and the second set of optical fibers is operatively coupled to a second laser and/or a second laser diode.

8. The catheter of claim 3, wherein the cutter comprises one or more blades, and wherein the cutter is positioned outside of an optical path of each of the first set of optical fibers and the second set of optical fibers.

9. The catheter of claim 1, wherein the laser radiation from the first set of optical fibers is configured to resect and/or ablate the undesired tissue located radially of the first set of optical fibers.

10. The catheter of claim 1, wherein the cutter is formed from a sharp distal edge of a wall of the distal end of the catheter.

11. A system for resecting an undesired tissue from a body of a subject, the system comprising:
    a catheter having:
      a distal end, a proximal end, a central longitudinal axis, and a central longitudinal lumen,
      a first set of optical fibers positioned about the central longitudinal axis between the distal end and the proximal end, wherein the first set of optical fibers are configured to transmit radiation in a first direction substantially transverse to the central longitudinal axis, and
      a cutter configured to cut the undesired tissue, the cutter having a distal end and a proximal end, wherein the proximal end of the cutter is positioned distally of the first set of optical fibers; and
    a suction source configured to be operatively coupled to the catheter and configured to generate a suction force through the central longitudinal lumen to collect the cut undesired tissue.

12. The system of claim 11, further comprising:
    a processor and a non-transitory computer-readable storage medium, the non-transitory computer-readable storage medium storing instructions that, when executed by the processor, cause the processor to control at least one of:
      a parameter of thermal radiation transmitted by the first set of optical fibers,
      a parameter of non-thermal radiation transmitted by the first set of optical fibers, and
      progression of the catheter relative to a target site within the body of the subject.

13. The system of claim 12, wherein the first set of optical fibers comprises a subset of optical fibers, and
    wherein the instructions, when executed by the processor, further cause the processor to control the subset of optical fibers to transmit the radiation in the first direction.

14. The system of claim 11, further comprising:
    a laser configured to be operatively coupled to the first set of optical fibers.

15. The system of claim 11, wherein the catheter further comprises:
    a second set of optical fibers positioned about the central longitudinal axis and configured to transmit radiation in a second direction substantially parallel to the central longitudinal axis.

16. The system of claim 15, wherein the cutter is positioned at least partially circumferentially inwardly or outwardly of the second set of optical fibers.

17. The system of claim 15, wherein the radiation from the second set of optical fibers is configured to resect and/or ablate the undesired tissue located distally of the second set of optical fibers.

18. The system of claim 15, wherein the first set of optical fibers and the second set of optical fibers are independently and selectively operable.

19. A system for resecting an undesired tissue from a body of a subject, the system comprising:
    a catheter having a tip section and a central longitudinal axis, the tip section comprising:
      a central longitudinal lumen,
      a cutter configured to cut the undesired tissue, the cutter comprising a cutter proximal end,
      a first set of optical fibers configured to transmit laser radiation in a first direction parallel to the central longitudinal axis, and a second set of optical fibers configured to transmit laser radiation in a second direction transverse to the central longitudinal axis, wherein the cutter proximal end is disposed a selected distance distally beyond the second set of optical fibers; and a suction source configured to be operatively coupled to the catheter and configured to generate a suction force through the central longitudinal lumen of the catheter to collect the cut undesired tissue therein.

\* \* \* \* \*